(12) United States Patent
Scarberry

(10) Patent No.: US 6,952,605 B1
(45) Date of Patent: Oct. 4, 2005

(54) PNEUMATIC RELEASE MECHANISM FOR A PATIENT CONTACTING ARTICLE

(75) Inventor: Eugene N. Scarberry, Trafford, PA (US)

(73) Assignee: Respironics, Inc., Murrysville, PA (US)

( * ) Notice: Subject to any disclaimer, the term of this patent is extended or adjusted under 35 U.S.C. 154(b) by 365 days.

(21) Appl. No.: 09/924,869

(22) Filed: Aug. 8, 2001

Related U.S. Application Data

(60) Provisional application No. 60/224,243, filed on Aug. 10, 2000.

(51) Int. Cl.[7] .............................................. A61B 5/04
(52) U.S. Cl. ..................... 600/372; 600/391; 600/392; 604/20
(58) Field of Search ................................ 600/391, 392, 600/394, 372, 395; 607/149, 152, 153; 604/20

(56) References Cited

U.S. PATENT DOCUMENTS

| | | | | |
|---|---|---|---|---|
| 2,882,904 A | * | 4/1959 | Rasmussen | .................. 607/155 |
| 3,295,515 A | * | 1/1967 | Kahn | .......................... 600/392 |
| 3,357,426 A | | 12/1967 | Cohen | |
| 3,420,223 A | * | 1/1969 | Day et al. | .................... 600/396 |
| 3,599,629 A | * | 8/1971 | Gordy | .......................... 600/392 |
| 3,602,216 A | * | 8/1971 | Moe, Jr. | ...................... 600/392 |
| 3,610,229 A | * | 10/1971 | Zenkich | ....................... 600/392 |
| 3,623,479 A | * | 11/1971 | Day | ............................. 600/372 |
| 3,713,435 A | * | 1/1973 | Szpur | .......................... 600/392 |
| 3,862,633 A | * | 1/1975 | Allison et al. | ............... 600/392 |
| 3,973,557 A | * | 8/1976 | Allison | ........................ 600/392 |
| 4,182,346 A | * | 1/1980 | Allison | ........................ 600/392 |
| 4,215,696 A | * | 8/1980 | Bremer et al. | ............... 600/392 |
| 4,267,840 A | * | 5/1981 | Lazar et al. | ................... 606/32 |
| 4,660,562 A | * | 4/1987 | House, Sr. | .................... 600/392 |
| 4,700,710 A | * | 10/1987 | Hoffman | ...................... 600/392 |
| 4,947,865 A | * | 8/1990 | Hon et al. | .................... 600/591 |
| 5,037,380 A | * | 8/1991 | Jacobsen et al. | .............. 604/20 |
| 5,124,076 A | * | 6/1992 | Smuckler | ................ 252/519.33 |
| 5,279,544 A | * | 1/1994 | Gross et al. | ................... 604/20 |
| 5,573,503 A | * | 11/1996 | Untereker et al. | ............. 604/20 |
| 5,820,572 A | | 10/1998 | Palmer | |
| 5,848,966 A | * | 12/1998 | Gusakov et al. | ............. 600/372 |
| 5,868,136 A | | 2/1999 | Fox et al. | |
| 5,983,131 A | * | 11/1999 | Weaver et al. | ................. 604/20 |
| 6,059,742 A | | 5/2000 | Palmer | |

\* cited by examiner

Primary Examiner—Gregory L. Huson
Assistant Examiner—Huong Q. Pham
(74) Attorney, Agent, or Firm—Michael W. Haas

(57) ABSTRACT

A patient contacting assembly comprising a patient contacting member that secures to the surface of a patient by means of an adhesive disposed between the patient contacting member and the patient. A channel is defined through the patient contacting member to enable a release fluid to be injected between the patient contacting member that the patient. Providing the release fluid between the patient contacting member and the patient at least partially reduces the bonding strength of the adhesive, making it easier to remove the patient contacting member from the patient and provides a pneumatic lift, urging the patient contacting member off of the surface of the patient.

13 Claims, 4 Drawing Sheets

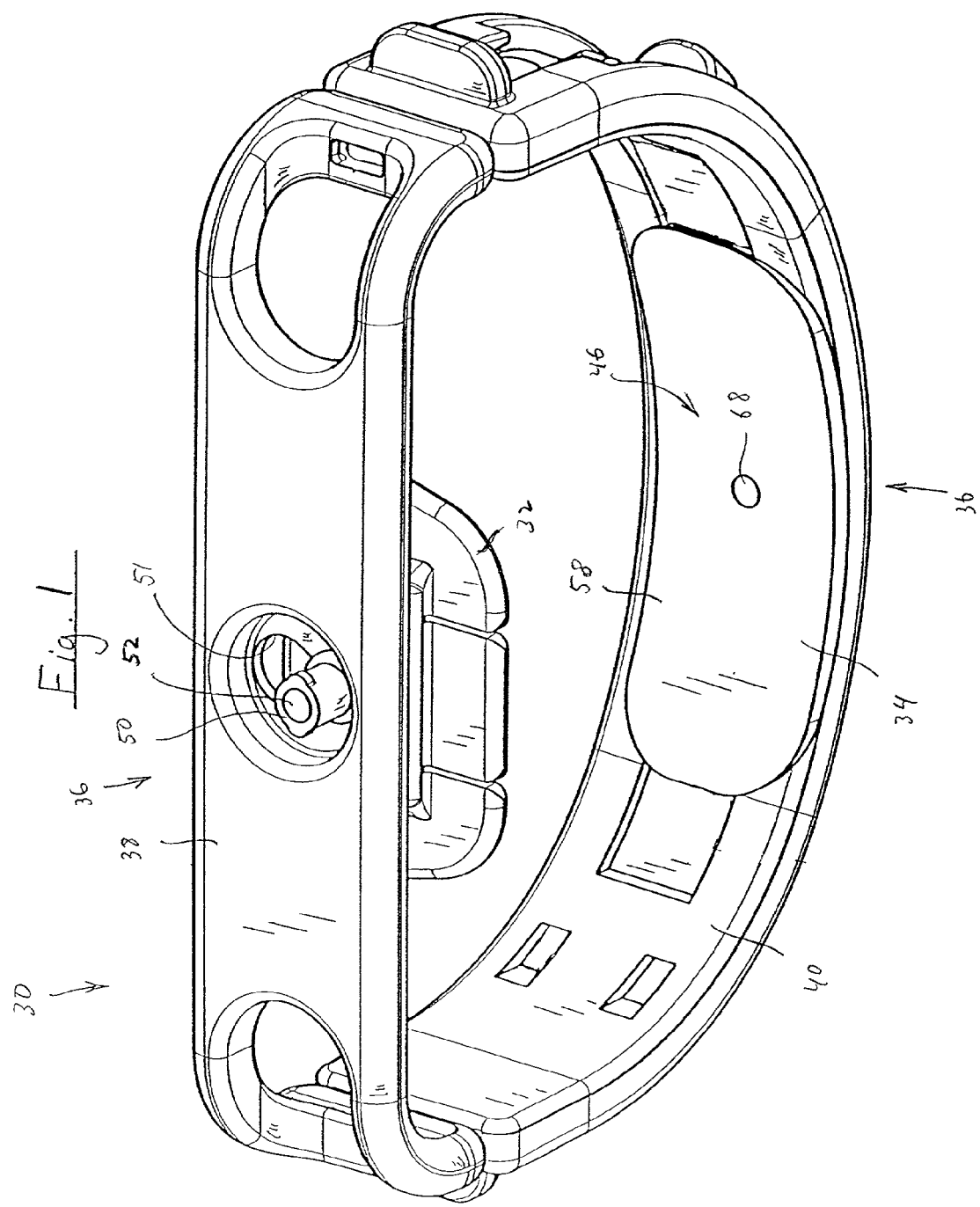

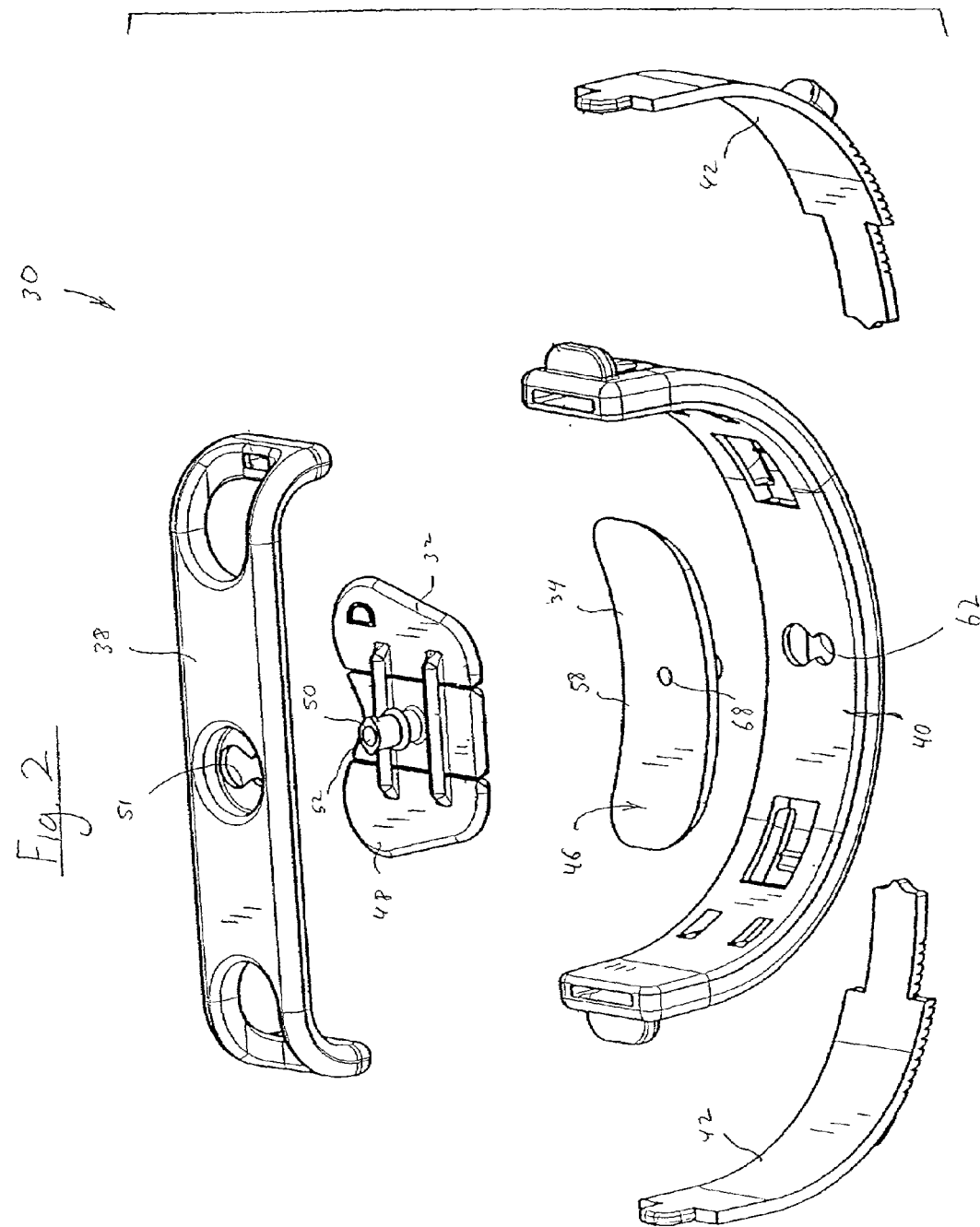

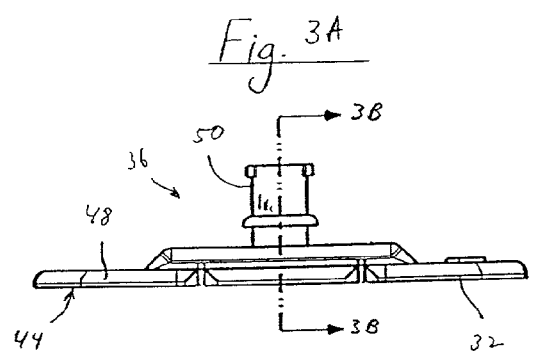
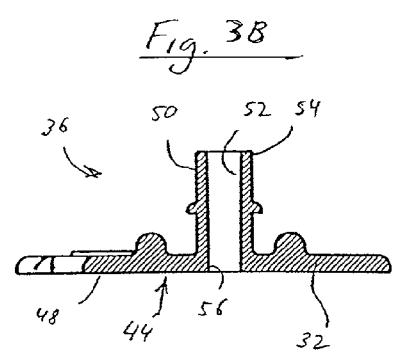
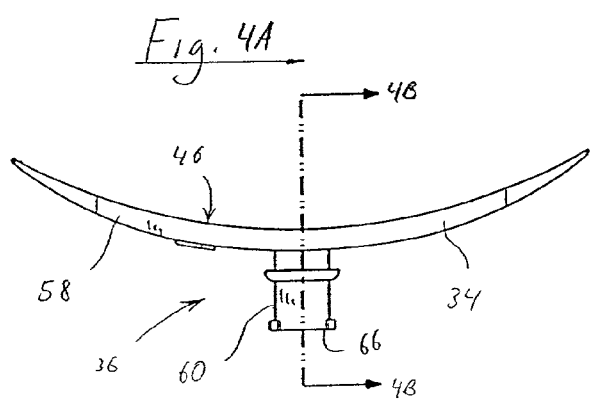
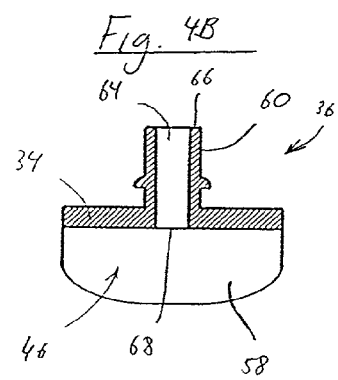

PNEUMATIC RELEASE MECHANISM FOR A PATIENT CONTACTING ARTICLE

This application claims the benefit of Provisional Application No. 60/224,243, filed Aug. 10, 2000.

BACKGROUND OF THE INVENTION

1. Field of the Invention

The present invention pertains to a patient contacting article including a pneumatic release mechanism for comfortably and safely disengaging the patient contacting article from the surface of the patient to which it is adhered. The present invention also pertains to a method of using such a pneumatic release mechanism.

2. Description of the Related Art

There are numerous situations where a medical implement must be securely, yet temporarily, affixed to the surface of a patient with an adhesive. U.S. Pat. No. 5,868,136 to Fox et al., for example, teaches a medical electrode that adhesively secures to the surface of the patient. Such medical electrodes can have a variety of configurations, sizes, and functions. These surface mounted medical electrodes are commonly used in an EKG, EMG, or EEG system to monitor electrical activity within a patient, typically requiring that they remain adhesively affixed to the patient for a relatively long period of time. Surface mounted electrodes are also used to deliver electrical energy to a patient. For example, a TENS device attempts to relieve pain by delivering small electrical impulses through electrodes placed on the skin to underlying nerve fibers. Electrical stimulation of the nerve fibers can block a pain signal from being carried to the brain and cause the body to releasing natural chemicals that act as analgesics.

Other situations in which a medical device must be securely and temporarily attached to a patient include the adherent face mask taught by U.S. Pat. No. 3,357,426 to Cohen. The mask taught by the '426 patent includes a relatively large, pliable peripheral edge that adheres to the patient's skin on the face and neck. The adhesive capability of the mask must be sufficient to prevent gas leakage at the mask-patient interface. U.S. Pat. Nos. 5,820,572 and 6,059,742 both to Palmer disclose a negative pressure chest brace in which the components of the brace are adhesively attach to the front and back of the patient's chest.

It can be appreciated that the adhesive used to secure a medical device or implement to a patient must be sufficiently strong to accomplish their intended function. For example, the adhesive used in chest brace apparatus must be sufficiently strong to allow the brace to apply a distending force on the patient. On the other hand, the adhesive must be capable of being removed from the patient relatively easily without damaging the patient's skin or tissues and with little or, preferably, no pain. This latter requirement can be especially difficult to meet in patients, such as infants, that have very delicate and sensitive skin. Often in conventional situations where a medical adhesive is used, the adhering strength is sacrificed in favor of providing an adhesive that can be easily and comfortably removed from the patient. Therefore, there is a need for an adhesive attachment technique that provides a strong degree of attaching capability without sacrificing ease and comfort when detaching the medical device or article from the patient.

SUMMARY OF THE INVENTION

Accordingly, it is an object of this invention to provide a patient contacting assembly that overcomes the shortcomings of conventional techniques for attaching a medical appliance to a patient. These objects, among others, are achieved, according to one embodiment of the present invention, by providing a patient contacting assembly that includes a patient contacting member having a first surface adapted to overly a portion of the patient. An adhesive secures the first surface to the surface of the patient. In addition, a channel is defined through the patient contacting member from a second surface to the first surface. The channel has a receiving end generally near the second surface enabling a release fluid to be introduced into the channel and a delivery end generally near the first surface. This channel communicates the release fluid to a location between the first surface and a surface of a patient to which the patient contacting member is adhered. The release fluid, at least partially, reduces the bonding strength of the adhesive, for example, by dissolving the adhesive, making it easier to remove the patient contacting member from the patient. In addition, injecting the release fluid between the patient and the patient contacting member provides a pneumatic lift, urging the patient contacting member off of the surface of the patient so that the patient contacting assembly can be easily and comfortably removed from the patient while minimizing, if not eliminating, tissue damage and pain.

It is a further object of the present invention to provide a method of selectively attaching a patient contacting assembly to a surface of a patient and detaching the assembly that overcomes the shortcomings of conventional adhesive securing techniques. This object is achieved by providing a method that includes: (1) providing a patient contacting member having a first surface and a second surface, (2) applying an adhesive to the first surface, the surface of the patient, or both, (3) securing the patient contacting member to a surface of the patient by contacting the first surface to the patient with the adhesive disposed therebetween; and (4) delivering a release fluid to a channel defined in the patient contacting member. The channel is configured and arranged to dispense the release fluid between the first surface and the surface of the patient to which the patient contacting member is adhered. As noted above, the release fluid at least partially reduces the bonding strength of the adhesive, making it easier to remove the patient contacting member from the patient and provides a pneumatic lift, urging the patient contacting member off of the surface of the patient so that the patient contacting assembly can be easily and comfortably removed from the patient.

These and other objects, features, and characteristics of the present invention, as well as the methods of operation and functions of the related elements of structure and the combination of parts and economies of manufacture, will become more in apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 1 and 2 are top and exploded perspective views, respectively, of a chest brace employing patient contacting assemblies that include a pneumatic release mechanism according to the principles of the present invention;

FIG. 3A is a side view of a chest plate patient contacting member used in the chest brace of FIGS. 1–2, and FIG. 3B is a cross-sectional view of the chest plate patient contacting member taken along line 3B—3B of FIG. 3A;

FIG. 4A is a side view of a back plate patient contacting member used in the chest brace of FIGS. 1–2, and FIG. 4B is a cross-sectional view of the back plate patient contacting member taken along line 4B—4B of FIG. 4A;

Figure 5A:
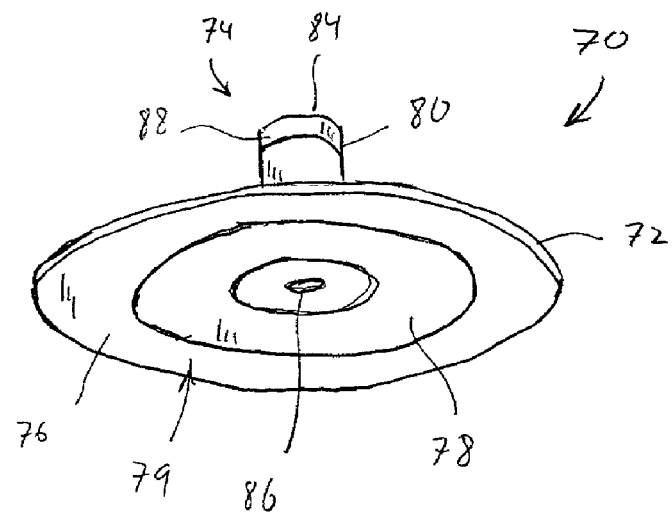
FIGS. 5A and 5B are perspective and cross-sectional views, respectively, of a medical electrode as a patient contacting member having a pneumatic release mechanism according to the principles of the present invention.

DETAILED DESCRIPTION OF THE PRESENTLY PREFERRED EXEMPLARY MBODIMENTS OF THE INVENTION

A chest brace 30 having a chest plate 32 and a back plate 34, each of which includes a pneumatic release mechanism, generally indicated at 36, according to the principles of the present invention, is shown schematically in FIGS. 1–4B. The details of chest brace 30 and its operation are set forth in co-pending U.S. Pat. No. 6,533,739, the contents of which are incorporated herein by reference. It is to be understood that the present invention is directed to the pneumatic release mechanism for selectively attaching a patient contacting assembly to a patient. In the embodiment illustrated in FIGS. 1–4B, the patient contacting assembly is chest plate 32 and back plate 34. However, other devices can function as the patient contacting assembly, as discussed below, for example, with reference to FIGS. 5A–6, which illustrates a medical electrode as the patient contacting assembly.

Referring again to FIGS. 1–4B, chest brace 30 includes an anterior member 38, a posterior member 40, and flexible linkages 42 that couple anterior member 38 and posterior member 40. Anterior member 38 is coupled to the patient via chest plate 32, and posterior member 40 is coupled to the patient via back plate 34. More specifically, a first surface 44 of chest plate 32 is adhesively secured to the patient's chest, and a first surface 46 of back plate 34 is adhesively secured to the patient's back. Chest plate 32 and back plate 34 are releaseably secured to anterior member 38 and posterior member 40, respectively. When positioned on a patient, the chest brace prevents collapse of the patient's chest walls and maintains the shape of the thorax. It can be appreciated that, in accomplishing these functions, a distending force is imparted on the patient by the chest and back plates, thereby requiring a relatively secure adhesive attachment between the patient and the chest and back plates. It should be further noted that the chest brace in the illustrated exemplary embodiment is intended to be used on infants, especially premature infants, which typically have delicate and fragile skin tissue. Therefore, it is also important that the chest and back plates be capable of being easily removed from such tissue, which a primary purpose of the pneumatic release mechanism of the present invention.

Chest plate 32 includes a relatively planar base 48, which acts a patient contacting member in that it is surface 44 of base 48 that adheres to the patient via an adhesive applied to surface 44, the surface of the patient, or both. In one embodiment of the present invention base 48 is a relative rigid member. It is to be understood, however, that the base, or portions thereof, can be made relatively flexible to make it easy for the base to contact the generally non-planar surface of the patient. A stem 50 attached to base 48 secures the chest plate to anterior member 38 in a slot and key configuration by interlocking in a channel 51 defined in the center of the anterior member. In the illustrated exemplary embodiment, stem 50 also serves as part of the pneumatic release mechanism, as discussed in greater detail below.

In a preferred embodiment of the present invention, a hydrogel adhesive of the type used conventionally to secure EKG electrodes to a patient is used as an adhesive material to bond surface 44 of chest plate 32 to the surface of the patient. A hydrogel adhesive, such as the hydrogel adhesive identified as RG73P and manufactured by Ludlow Technical Products of Huntington Beach, Calif., which is a water-based adhesive, is preferred because, as a hydrogel, it dissolves or has reduced adhering capability when flushed with water or a saline solution. Therefore, the adhesive can easily removed from the patient with a minimal amount of tissue damage and pulling using only water as a solvent. Although a water-based hydrogel is believed to be preferably due to its biocompatibility with human tissue, the present invention also contemplates using other types of hydrogels, such as oil-based adhesives, to secure the back plate and chest plate to the surface of the patient.

To facilitate detachment of the chest plate from the patient, pneumatic release mechanism 36 incorporated into chest plate 32 includes a channel 52 is defined in stem 50. One end 54 of channel 52 is adapted to receive a liquid, preferably a solvent capable of dissolving or reducing the adhesive strength of the hydrogel, so that the liquid can be inserted into the channel. A second end 56 of channel 52 is provided at surface 44 so that the liquid injected into the channel can be delivered between surface 44 and the surface of the patient. The insertion of such a liquid between surface 44 and the surface of the patient also provides a pneumatic release mechanism tending to urge surface 44 and the surface of the patient apart. That is, a liquid injected between the patient and surface 44 tends to dislodge or lift surface 44 from the patient in a pneumatic fashion.

Back plate 34 is similar to chest plate 32 except that back plate 34 includes a base 58 that is curved to match the general curvature of the back of the patient, unlike base 48. A stem 60 attached to base 58 secures the back plate to posterior member 40 in a slot and key configuration by interlocking in a channel 62 defined in the center of the posterior member. As with the chest plate, stem 60 also serves as part of the pneumatic release mechanism in that the stem includes a channel 64. Surface 46 of base 58 adheres to the back of the patient, preferably using the above-described hydrogel adhesive.

Like stem 50 in chest plate 32, stem 60 of back plate 38 includes a channel 64 so that a liquid, preferably a solvent, can be inserted into a first end 66 of the channel and delivered to an opening 68 in a second end of the channel so that the liquid is discharged between surface 46 and the surface of the patient. As noted above, the insertion of such a liquid between surface 46 and the surface of the patient assists in dissolving or reducing the strength of the adhesive securing surface 46 to the patient and provides a pneumatic release mechanism tending to urge surface 46 and the surface of the patient apart.

In the embodiment illustrated in FIGS. 1–4B, at least a portion of the channel that carries the release fluid to surface of the patient is defined in a stem attached to the base. It is to be understood, however, that channel need not be provided in the stem. Rather, a channel can be provided at any one of a variety of locations on the base, so long as the channel communicates the release fluid to a location between surface 44 or 46. Furthermore, if provided in the stem, the channel need not run generally parallel to the stem. Also, other openings can be provided along the stem into which the release fluid can be injected. It is to be further understood that a plurality of channels, with or without a stem, can be provided at other locations on the base. Providing multiple channels and injecting the release fluid into such channels maximized the distribution of the release fluid over the area of surface 44 or 46. Additional channels may also be necessary or desirable depending on the geometry of the patient contacting member to ensure that the release fluid is delivered to the appropriate areas of the patient contacting member.

Figure 5B:
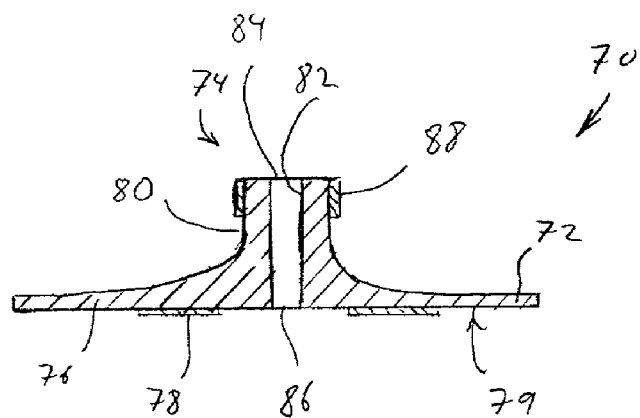

As noted above, the present invention contemplates that a variety of devices can function as the patient contacting member for use with the pneumatic release mechanism. FIGS. 5A–5B illustrate a patient contacting assembly 70 in which a medical electrode 72 is the patient contacting member that operates in conjunction with a pneumatic release mechanism, generally indicated at 74, according to the principles of the present invention.

Patient contacting assembly 70 includes a substrate 76 to which an electrode 78 is attached. It is to be understood that electrode 78 can be attached to the substrate, imbedded in the substrate, or secured at other locations on the substrate and in any manner known to those skilled in the art. In this illustrated embodiment, electrode 78 is attached to a surface 79 of the substrate. A stem 80 is provided on an opposing surface. As in the previous embodiments, a channel 82 is defined in stem 80 enabling a release liquid injected in a first end 84 to be dispensed from a second end 86 of the channel and disposed between surface 79 and a surface of a patient to which the substrate is attached (not shown).

In the illustrated embodiment, stem 80 is integral with substrate 72. However, this need not be the case, as each element of the patient contacting member can be formed separately, out of different materials if desired, and affixed to one another during the manufacturing process in any conventional manner. The same is true for stems 50 and 60 of FIGS. 1–4B. Stem 80 in the embodiment illustrated in FIGS. 5A–5B serves dual functions. As noted above, stem 80 provides a channel into which the release fluid is injected using a syringe, for example. Stem 80 can also serve as a contact terminal for an electrical connection between an external lead wire and electrode 78.

The illustrated embodiment, for example, provides a contact terminal 88 at first end 84 so that an electrical lead (not shown) can be operatively connected to electrode 78 by means of selective attachment to contact 88. Although not shown in FIGS. 5A–5B, an electrical connection is provided between contact 88 and electrode 78. This electrical connection can be provided through channel 82. Of course, stem 80 can be eliminated, channel 82 provided only within substrate 72, and an electrical contact can be provided using any conventional technique.

Figure 6:
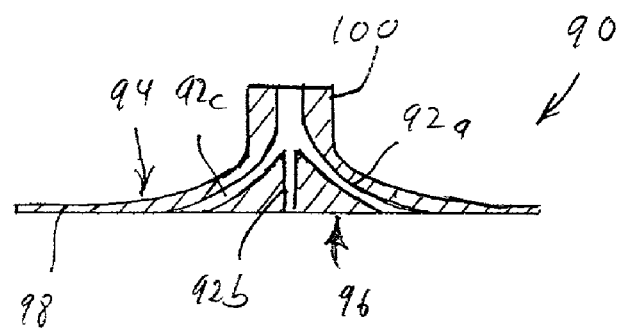
FIG. 6 is a cross-sectional view of a medical electrode having a pneumatic release mechanism according to a further embodiment of the present invention.

FIG. 6 is a cross-sectional view of a patient contacting assembly 90 in which the patient contact member is also a medical electrode. In this embodiment, however, the pneumatic release mechanism includes multiple channels 92a, 92b, 92c defined in the substrate 98 from a first surface 94 to a second surface 96 thereof. The use of multiple channels helps ensure that the release fluid is more completely distributed over the area of second surface 96. In this embodiment, channels 92a–92c branch off of a main channel in stem 100. It is to be understood, however, that the channels can be provided at other locations throughout the substrate and need not be provided in the stem. In addition, each channel can have multiple branches.

The pneumatic release mechanism of the present invention can be used, for example, with a medical mask (nasal, oral, or both), such as the mask taught by U.S. Pat. No. 3,357,426 to Cohen. The pneumatic release mechanism can also be used with a medical adhesive strip or tape making it easier to remove same. As noted above, the pneumatic release mechanism can be used with a traction or brace device in which a portion of the device is adhered to the surface of a patient, such as the chest brace taught by U.S. Pat. Nos. 5,820,572 and 6,059,742 both to Palmer. Other applications for the pneumatic release mechanism include a dental appliance, a prostheses, or any situation where a material, element or other components is removeably affixed to the tissue of a patient.

The present invention also contemplates that the pneumatic release mechanism of the present invention has non-medical applications. For example, in the make-up, special effects, or cosmetic industry, there is often a need to adhere an appliance to an actor or user. For example, it is known to apply a silicon appliance to an actor's face to alter his or her facial features. A biocompatible adhesive is typically used to secure the appliance to the actor. The present invention contemplates providing a pneumatic release mechanism on the appliance so that it can be more easily removed. It is to be understood that the above list of potential applications for the pneumatic release mechanism is intended to be exemplary of the situations where such a release mechanism may have merit. It is not intended to represent a complete or exclusive catalog of all such applications. On the contrary, the present invention contemplates that the pneumatic release mechanism of the present invention is applicable to in any situation where an element is to be releaseably secured to a person or animal.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient contacting assembly, comprising:
   a patient contacting member including a first surface adapted to overlie a portion of a patient and a second surface;
   an adhesive disposed on the first surface and adapted to secure the first surface to a surface of such a patient;
   a stem having a first end portion operatively coupled to the second surface of the patient contacting member and an exposed second end portion; and
   a channel defined through the stem from the first end portion to the second end portion and defined through the patient contacting member from the second surface to the first surface, wherein the second end portion of the stem is adapted to receive a release fluid for introduction into the channel, wherein the channel communicates the release fluid proximate to the first surface so as to dispense such a release fluid from the channel between the first surface and a surface of a patient to which the patient contacting member is adhered, wherein the channel is sized and configured such that introducing the release fluid into the channel urges the first surface and the surface of the patient apart, thereby dislodging the patient contacting assembly from the patient in a pneumatic fashion, and wherein the channel includes multiple branches emanating from the channel to disperse the release fluid over an area of the first surface.

2. The patient contacting assembly according to claim 1, wherein the adhesive is a hydrogel adhesive disposed on the first surface or a surface of a patient.

3. The patient contacting assembly according to claim 1, wherein the stem is integral with the patient contacting member.

4. The patient contacting assembly according to claim 1, further comprising an electrode provided on the first surface of the patient contacting member.

5. The patient contacting assembly according to claim 1, further comprising means, associated with the patient contacting member, for applying a distending force on a surface of a patient to which the patient contacting member is adhered.

6. The patient contacting assembly according to claim 1, wherein the patient contacting member is defined, at least in party, by a substantially rigid material.

7. A patient contacting assembly comprising:
a patient contacting member including a first surface adapted to overlie a portion of a patient and a second surface;
adhering means for securing the first surface to a surface of such a patient;
a stem having (a) a first end portion operatively coupled to the second surface of the patient contacting member and (b) an exposed second end portion; and
releasing means associated with the patient contacting member and the stem for delivering a release fluid, which is introduced into second end portion of the stem, to a location between the first surface and a surface of a patient to which the patient contacting member is adhered, wherein the release means is sized and configured such that introducing the release fluid into the stem urges the first surface and the surface of the patient apart, thereby dislodging the patient contacting assembly from the patient in a pneumatic fashion, and wherein the release means includes (i) a channel defined in the stem and (ii) a plurality of branches emanating from the channel to disperse the release fluid over an area of the first surface.

8. The patient contacting assembly according to claim 7, wherein the adhering means is a hydrogel adhesive.

9. The patient contacting assembly according to claim 7, further comprising means, associated with the patient contacting member, for applying a distending force on a surface of a patient to which the patient contacting member is adhered.

10. A method of selectively attaching a patient contacting assembly to a surface of a patient and detaching same, comprising:
providing a patient contacting member having a first surface, a second surface, and a stem operatively coupled to the second surface of the patient contacting member and extending therefrom such that an end of the stem is exposed;
providing an adhesive on the first surface, a surface of a patient to which the patient contacting assembly is to be attached, or both;
securing the patient contacting member to a surface of a patient by contacting the first surface to such a surface of a patient with the adhesive disposed therebetween; and
delivering a release fluid to a channel defined in the patient contacting member and the stem by introducing the release fluid into an exposed end of the stem, wherein the channel includes a plurality of branches emanating from the channel to dispense the release fluid from the channel between the first surface and a surface of a patient to which the patient contacting member is adhered, and wherein the release fluid is delivered to the channel in a manner that causes the release fluid to impart a pneumatic force on the first surface and the surface of the patient urging them part, thereby dislodging the patient contacting assembly from the patient in a pneumatic fashion.

11. The method according to claim 10, wherein delivering a release fluid includes injecting a solvent adapted to reduce a bonding strength of the adhesive into the channel as the release fluid.

12. The method according to claim 11, wherein the adhesive is a hydrogel adhesive, and wherein delivering a release fluid includes injecting water or a saline solution into the channel as the release fluid.

13. The method according to claim 10, wherein delivering a release fluid includes injecting the release fluid via a syringe into the channel.

* * * * *